(12) United States Patent
Case (10) Patent No.: US 8,303,647 B2
(45) Date of Patent: Nov. 6, 2012

(54) MEDICAL VALVE LEAFLET STRUCTURES WITH PERIPHERAL REGION RECEPTIVE TO TISSUE INGROWTH

(75) Inventor: Brian C. Case, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 925 days.

(21) Appl. No.: 11/367,979

(22) Filed: Mar. 3, 2006

(65) Prior Publication Data

US 2006/0253188 A1    Nov. 9, 2006

Related U.S. Application Data (60) Provisional application No. 60/658,326, filed on Mar. 3, 2005.

(51) Int. Cl.
*A61F 2/06* (2006.01)
(52) U.S. Cl. ............... 623/1.24; 623/1.26; 623/2.12; 623/2.13; 623/2.14
(58) Field of Classification Search ............... 623/1.24, 623/1.26, 2.12, 2.13, 2.14
See application file for complete search history.

(56) References Cited

U.S. PATENT DOCUMENTS

| | | | |
|---|---|---|---|
| 4,218,782 A | 8/1980 | Rygg | |
| 4,675,361 A | 6/1987 | Ward | |
| 4,861,830 A | 8/1989 | Ward | |
| 4,902,508 A | 2/1990 | Badylak et al. | |
| 5,156,620 A | 10/1992 | Pigott | |
| 5,411,552 A | 5/1995 | Andersen et al. | |
| 5,554,389 A | 9/1996 | Badylak et al. | |
| 5,607,465 A | 3/1997 | Camilli | |
| 5,855,601 A | 1/1999 | Bessler et al. | |
| 6,110,201 A | 8/2000 | Quijano et al. | |
| 6,126,686 A | 10/2000 | Badylak et al. | |
| 6,168,614 B1 | 1/2001 | Andersen et al. | |
| 6,200,336 B1 | 3/2001 | Pavcnik et al. | |
| 6,206,931 B1 | 3/2001 | Cook et al. | |
| 6,287,334 B1 | 9/2001 | Moll et al. | |
| 6,299,637 B1 | 10/2001 | Shaolian et al. | |
| 6,440,164 B1 * | 8/2002 | DiMatteo et al. | ............ 623/1.24 |
| 6,508,833 B2 | 1/2003 | Pavcnik et al. | |
| 6,582,462 B1 | 6/2003 | Andersen et al. | |
| 6,666,885 B2 | 12/2003 | Moe | |
| 6,685,739 B2 * | 2/2004 | DiMatteo et al. | ............ 623/1.24 |
| 6,716,241 B2 | 4/2004 | Wilder et al. | |
| 6,752,828 B2 | 6/2004 | Thornton | |
| 6,840,957 B2 * | 1/2005 | DiMatteo et al. | ............ 623/1.24 |
| 7,267,686 B2 * | 9/2007 | DiMatteo et al. | ............ 623/1.24 |
| 2001/0011187 A1 | 8/2001 | Pavcnik et al. | |

(Continued)

FOREIGN PATENT DOCUMENTS

WO    WO 01/19285    3/2001

(Continued)

*Primary Examiner* — Thomas J Sweet
*Assistant Examiner* — Christopher D Prone
(74) *Attorney, Agent, or Firm* — Woodard, Emhardt, Moriarty, McNett & Henry LLP (57) ABSTRACT

Composite leaflets and prosthetic valves incorporating the same are disclosed. An illustrative composite leaflet includes a flexible inner region, which is formed with a synthetic polymeric material, and a flexible peripheral region, which is formed with a remodelable material effective to promote tissue ingrowth. The peripheral region extends from at least a portion of the flexible inner region and is configured to contact a wall of a tubular body passage and thereby promote tissue ingrowth into the peripheral region from the wall of the tubular body passage.

28 Claims, 9 Drawing Sheets

U.S. PATENT DOCUMENTS

| | | |
|---|---|---|
| 2001/0039450 A1 | 11/2001 | Pavcnik et al. |
| 2002/0065552 A1 | 5/2002 | Jayaraman et al. |
| 2002/0123800 A1 | 9/2002 | Taheri et al. |
| 2002/0188348 A1 | 12/2002 | DiMatteo et al. |
| 2003/0036795 A1 | 2/2003 | Andersen et al. |
| 2003/0055496 A1 | 3/2003 | Cai et al. |
| 2003/0118560 A1* | 6/2003 | Kelly et al. .................. 424/93.7 |
| 2003/0130726 A1 | 7/2003 | Thorpe |
| 2003/0191525 A1 | 10/2003 | Thornton |
| 2003/0208261 A1 | 11/2003 | Thorpe et al. |
| 2004/0015230 A1 | 1/2004 | Moll et al. |
| 2004/0024452 A1* | 2/2004 | Kruse et al. .................. 623/2.13 |
| 2004/0049262 A1 | 3/2004 | Obermiller et al. |
| 2004/0088046 A1 | 5/2004 | Speziali |
| 2004/0193253 A1 | 9/2004 | Thorpe et al. |
| 2005/0021136 A1* | 1/2005 | Xie et al. ..................... 623/2.14 |
| 2006/0190074 A1* | 8/2006 | Hill et al. ..................... 623/1.23 |

FOREIGN PATENT DOCUMENTS

| | | |
|---|---|---|
| WO | WO 03/070124 | 8/2003 |
| WO | WO 2004/082528 | 9/2004 |

* cited by examiner

MEDICAL VALVE LEAFLET STRUCTURES WITH PERIPHERAL REGION RECEPTIVE TO TISSUE INGROWTH

REFERENCE TO RELATED APPLICANTS

This application claims the benefit of U.S. Provisional Patent Application No. 60/658,326 filed Mar. 3, 2005, which is hereby incorporated herein by reference in its entirety.

BACKGROUND

The present invention relates to prosthetic devices, and in certain embodiments, to prosthetic valve leaflets that have a peripheral region receptive to tissue ingrowth.

It is well understood in human pathology that the proper functioning of cardiac and venous valves is of the utmost importance. Numerous studies have shown that diseased cardiac valves cause significant morbidity and mortality and that incompetent or destroyed venous valves often result in adverse medical conditions, especially in the lower extremities.

By preventing retrograde blood flow, the valves found throughout the venous system assist the flow of blood through the veins and returning to the heart. Venous valves are usually of the bicuspid type, with each cusp or leaflet forming a reservoir for blood, which, under pressure, forces the free edges of the cusps together to permit mostly antegrade blood flow to the heart. As a majority of venous blood flow is against gravity while a person is standing, incompetent or destroyed venous valves can cause significant medical problems in the legs, ankles, and feet. There are at least two chronic venous diseases in which venous valve incompetence is thought to be an important factor: chronic venous insufficiency and varicose vein syndrome.

Chronic venous insufficiency involves venous hypertension and chronic venous stasis due to valvular incompetence. In the United States, it has been estimated that chronic venous insufficiency (CVI) associated with skin changes and ulcers affects six to seven million people. Existing treatments for chronic venous insufficiency are less than ideal. Therapies currently available include periodic elevation of the legs, elastic support hose to compress the veins externally, and surgical repair or replacement of the valves by grafting veins from the patient's arm into the leg. These methods are variably effective. Similarly, the palliative therapies require major lifestyle changes for the patient with potentially suboptimal long-term patient compliance. Also, without repairing the valves, even if the ulcers are healed, the ulcers will recur unless the patient continues to elevate the legs and to use support hose continuously.

Varicose vein syndrome, a second chronic venous disease, involves vein dilation or enlargement. According to one estimate, varicose veins affect about 4% of the adult western population, and approximately half of this population has significant varicose vein syndrome for which treatment will be sought.

Turning now to the cardiovascular system, incompetent or destroyed heart valves are a common form of heart disease, the leading cause of death in the United States. Although reconstructive surgery has been shown to be superior to valve replacement surgery in some respects, it is difficult to perform and not always possible in every patient. As a result, the vast majority of patients with diseased heart valves undergo valve replacement surgery, which involves removing a native valve and replacing it with a prosthetic one. Prosthetic heart valves come in various shapes and sizes and can be formed with a variety of materials. Often, the design of a prosthetic valve depends on the characteristics of the valve being replaced (e.g., mitral, aortic, tricuspid, or pulmonary) and/or the size of the patient's heart.

A variety of prosthetic valves have been developed in the art to treat conditions of the cardiovascular and venous systems. One such valve is defined by a tubular wall and one or more flexible leaflets. The leaflets are integrally connected to the tubular wall and converge axially along at least one commissure. The leaflets are designed to open and close the valve in response to pressure differentials across the valve. In an open, flow-conducting configuration, the free edges of adjacent leaflets are forced apart to form a conduit through which blood can flow. In a closed, flow-restricting configuration, the free edges of adjacent leaflets are forced together to form a closure, which eliminates or greatly reduces back flow through the valve.

There remain needs for improved and/or alternative prosthetic devices, and in particular prosthetic valve leaflets, suitable for implantation in a body vessel. The present invention is addressed to those needs.

SUMMARY

The present invention provides, in certain aspects, unique medical valve leaflet structures that include regions having material properties that differ from one another. Illustratively, certain embodiments of the present invention relate to implantable prosthetic valves that include one or more leaflets that have first and second regions that differ from one another relative to their propensity for receiving and/or promoting tissue ingrowth. For example, a first region of the leaflet can be configured for extending into a lumen of a bodily passage, and a second region can be configured for contact with a wall of the bodily passage and can have a greater ability to receive and/or promote tissue ingrowth than the first region. The second region can thus serve to facilitate beneficial attachment or integration of the leaflet structure with the wall of the bodily passage, and the first region can be optimized for other function(s), e.g. to serve as a functional portion of a flexible leaflet extending into the bodily passage lumen and participating alone or with one or more additional such leaflets in a coapting arrangement in response to fluid flow in the bodily passage.

In one particular embodiment, the invention provides a medical valve leaflet for implantation in a tubular body passage. The leaflet includes a flexible inner region, which is formed with a synthetic polymeric material, and a flexible peripheral region, which is formed with a remodelable material to promote tissue ingrowth. The peripheral region extends from at least a portion of the flexible inner region and is configured to contact a wall of the tubular body passage and thereby promote tissue ingrowth into the peripheral region from the wall of the tubular body passage.

Another embodiment of the present invention provides a valve prosthesis that includes one or more composite leaflets attached to a frame. Each leaflet includes a flexible inner region, which is formed with a synthetic polymeric material, and a flexible peripheral region, which is formed with a remodelable material to promote tissue ingrowth. The peripheral region extends from at least a portion of the flexible inner region and is configured to contact a wall of the tubular body passage and thereby promote tissue ingrowth into the peripheral region from the wall of a tubular body passage.

Yet another embodiment of the invention provides a medical valve leaflet that includes a first segment and a second segment. The first segment has a first segment boundary portion, and the second segment has a second segment boundary portion. The second segment boundary portion is attached to the first segment boundary portion. Both segments can be formed with a variety of materials. For example, the first segment can be formed with a synthetic polymeric material, while the second segment can be formed with a remodelable material, such as small intestinal submucosa. The second segment boundary portion can be configured to contact a wall of a tubular body passage and thereby promote tissue ingrowth into the second segment from the wall of the tubular body passage.

A further embodiment of the invention provides a method of manufacturing a medical valve leaflet. The leaflet is manufactured by providing a first segment, which has a first segment boundary portion, and a second segment, which has a second segment boundary portion. At least a portion of the first segment boundary portion is then attached to at least a portion of the second segment boundary portion. Various modes of attachment may be used, including but not limited to suturing, vacuum pressing, and bonding.

Another embodiment of the present invention provides a valve prosthesis that includes one or more composite leaflets attached to a frame. Each leaflet includes a first segment, which has a first segment boundary portion, and a second segment, which has a second segment boundary portion. For each leaflet, at least a portion of the leaflet's first segment boundary portion is attached to at least a portion of the leaflet's second segment boundary portion. Each leaflet's second segment can be configured to contact a wall of a tubular body passage and thereby promote tissue ingrowth into that second segment from the wall of the tubular body passage.

Yet another embodiment of the present invention provides a method of treating a patient. The method includes providing a prosthetic valve and then implanting it into a bodily passageway of a patient. The prosthetic valve comprises a frame and one or more leaflets attached to the frame. Each leaflet includes a first segment and a second segment. The second segment of each leaflet extends from at least a portion of that leaflet's first segment. Each leaflet's second segment can be configured to contact a wall of a tubular body passage and thereby promote tissue ingrowth into the second segment from the wall of the tubular body passage.

In another embodiment, the invention provides a medical valve leaflet for implantation in a tubular body passage, wherein the leaflet includes a flexible inner region, which is formed with a non-remodelable material, and a flexible peripheral region, which is formed with a remodelable material to promote tissue ingrowth. The peripheral region extends from at least a portion of the flexible inner region and is configured to contact a wall of the tubular body passage and thereby promote tissue ingrowth into the peripheral region from the wall of the tubular body passage.

In yet another embodiment, the invention provides a medical valve leaflet for implantation in a tubular body passage. The leaflet includes a flexible inner region, which is formed with a synthetic polymeric material, and a flexible peripheral region, which is formed with a material to promote tissue ingrowth. The peripheral region extends from at least a portion of the flexible inner region and is configured to contact a wall of the tubular body passage and thereby promote tissue ingrowth into the peripheral region from the wall of the tubular body passage.

Other objects, embodiments, forms, features, advantages, aspects, and benefits of the present invention shall become apparent from the detailed description and drawings included herein.

DETAILED DESCRIPTION

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

Valve prosthesis devices can be used to replace and/or supplement incompetent or destroyed cardiac or venous valves in mammals or to otherwise beneficially modify fluid flow in a bodily passage. The present invention, illustrative examples of which are illustrated in FIGS. 1-12, provides improved and/or alternative prosthetic valves, as well as unique leaflet arrangements that can be implanted into a tubular body passage of a patient, especially a human, including for example in veins or arteries.

Figure 1:
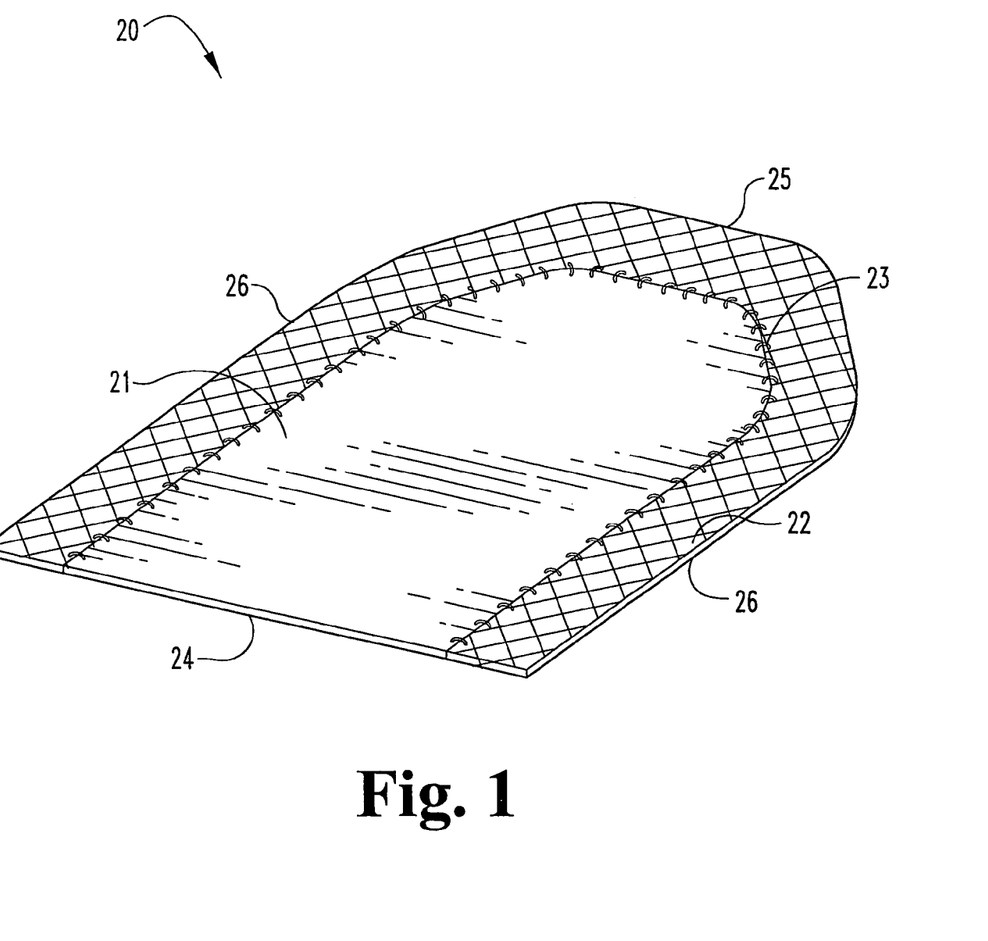
FIG. 1 is a perspective view of a medical valve leaflet that has a peripheral region extending from an inner region.

Referring now to the drawings, FIG. 1 is a perspective view of a medical valve leaflet 20 that has a flexible inner region 21 and a flexible peripheral region 22. The peripheral region 22 extends from at least a portion of the inner region 21, and the two regions are attached with sutures 23. The leaflet 20 has a first end 24, a second end 25, and sides 26. Portions of the inner region 21 and peripheral region 22 form the leaflet's first end 24, while at least a portion of the peripheral region 22 forms the leaflet's second end 25 and sides 26. The size and shape of the inner region 21 and peripheral region 22 can vary depending on the size and shape of the leaflet 20 being assembled. Again, the leaflet 20 should be suitable for implantation into a tubular body passage (e.g., a vessel or duct) of a patient.

The materials used to form the composite leaflets of the present invention should generally be biocompatible. In certain embodiments, a leaflet peripheral region is comprised of a tissue ingrowth-receptive material, while a leaflet inner region is comprised of a material that is relatively less receptive to tissue ingrowth or not receptive at all. Such peripheral regions may be formed with one or more of a variety of suitable tissue ingrowth materials including reconstituted and naturally-derived collagenous materials. In some aspects of the invention, such materials that are bioremodelable and promote cellular invasion and ingrowth will provide particular advantage.

Suitable bioremodelable materials can be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multiaxial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

For the leaflet 20 of FIG. 1, the peripheral region 22 is formed with a remodelable extracellular matrix (ECM) material that is effective to promote tissue ingrowth. In addition to providing desired flexibility and acceptable fluid dynamic performance, ECM material may include a bioactive component that has the capacity to induce host tissue proliferation and lead to the remodeling and regeneration of tissue structures upon in vivo implantation. Thus, remodelable ECM material is particularly suitable for forming the peripheral region 22, since the peripheral region 22 is configured to contact a wall of a tubular body passage and thereby promote tissue ingrowth into the peripheral region 22 from the wall of the tubular body passage.

The inner region 21 of the device illustrated in FIG. 1, on the other hand, is not formed with a remodelable material. In certain embodiments, for example, the inner region 21 is formed with a synthetic polymeric material. Illustratively, a synthetic polymer can be selected based on its ability to prevent the inner region 21 from adhering or fusing to another leaflet or the wall of a tubular body passage and/or its ability to resist calcification. Calcification of the inner region 21 may result in loss of flexibility or improper closure and/or opening of the valve after implantation.

The leaflet 20 has a variety of uses, including but not limited to replacing one or more of a native valve's leaflets, or forming part of a prosthetic valve, which can then be used to replace an incompetent or destroyed native valve (or another prosthetic valve) of the cardiovascular or venous systems. Regardless of the application, the leaflet 20 is designed to help open and close a valve in response to changes in fluid dynamic pressure across the valve.

The leaflet 20 can be incorporated into a variety of prosthetic valves. For example, in certain embodiments, the leaflet 20 is used to form part of a bi-leaflet valve. In this case, at least a portion of the leaflet's second end 25 and sides 26 can be attached to a support structure and/or a wall of a tubular body passage, leaving the first end 24 extending into the lumen of the bodily passage and generally free to move back and forth to participate in opening and closing the valve. Thus, with the bi-leaflet valve in an open, flow-conducting configuration, the leaflets' first ends 24 are generally forced away from each other and toward the vein wall to form a conduit therethrough for blood to flow. In a closed, flow-restricting configuration, the leaflets' first ends 24 are generally forced away from the vein wall and toward each other to form a closure (or coaptation) to eliminate or greatly reduce back flow through the valve.

An inner region of an invention leaflet may be formed with one or more of a variety of suitable biocompatible materials. Illustratively, a variety of synthetic polymeric materials can be used to form the flexible inner region 21 depicted in FIG. 1, including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary valve function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate. The material may be in the form of yarns, fibers, and/or resins, monofilament yarns, high tenacity polyester. Further, the present application contemplates other plastic, resin, polymer, woven, and fabric surgical materials, other conventional synthetic surgical materials, such as a shape-memory plastic, and/or combinations of such materials.

A variety of biocompatible polyurethane materials can be used in the present invention. One such material is THORALON® (THORATEC, Pleasanton, Calif.), described in U.S. Pat. Application Publication No. 2002/0065552 A1 and U.S. Pat. No. 4,675,361, both of which are incorporated herein by reference. The biocompatible polyurethane material sold under the tradename THORALON is a polyurethane base polymer (referred to as BPS-215) blended with a siloxane containing surface modifying additive (referred to as SMA-300). The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

Various forms of THORALON may be utilized in the present invention, and in this regard, a particular THORALON material may be selected based on one or more characteristics of the material such as but not limited to its ability to inhibit thrombosis, tensile strength, resistance to water absorption, critical surface tension, flexibility, flex life and the like.

Additionally, THORALON can be formed as a porous or non-porous material. When used in the present invention, porous THORALON materials can have varying degrees of porosity, varying pore sizes, etc. In some embodiments, inventive devices incorporate two or more different types of THORALON material. For example, a leaflet can have an inner region comprised of a non-porous form of THORALON that is not receptive to tissue ingrowth and a peripheral region comprised of a porous form of THORALON that is receptive to tissue ingrowth. Alternatively, one or more leaflets of a valve device can include an inner region (e.g. 21) comprising such polyurethane materials or modified forms thereof, and an outer region comprising a remodelable material, as described herein.

Continuing with FIG. 1, the remodelable material used to form the peripheral region 22 of the illustrated device can be formed with, for example, a generally intact, native tissue segment (e.g., tissue from a porcine aortic valve), which has been extracted from a warm-blooded vertebrate and subsequently processed to form a suitable tissue segment. The peripheral region 22 can also be formed with an extracellular matrix (ECM) material, such as small intestinal submucosa (SIS).

Remodelable ECM material for use in the present invention can be derived from a variety of natural sources, including pericardial tissues (e.g., pericardial sacs), amniotic sacs, connective tissues, dermal tissue, blood vessels, dura mater, fascia, umbilical tissues, renal capsule membrane, serosa, peritoneum, basement membrane materials (e.g., liver basement membrane), submucosa and the like. Biological materials can be derived from a particular animal species, typically mammalian, such as human, bovine, equine, ovine, or porcine. Moreover, suitable biological tissues include xenografts (i.e., cross species, such as a non-human donor for a human recipient), allografts (i.e., intraspecies with a donor of the same species as the recipient) and autografts (i.e., the donor and the recipient being the same individual). Suitable biological tissue is generally soft tissue. In certain embodiments, the biological material is fully or partially crosslinked as discussed in detail below.

Submucosal tissue of cattle, sheep, and other warm-blooded vertebrates, especially pigs, provides a particularly preferred material for use in the present invention. A favorable characteristic of remodelable submucosal tissue (e.g., small intestinal submucosa, stomach submucosa, urinary bladder submucosa, or uterine submucosa) is that it has the capacity to induce host tissue proliferation. Accordingly, submucosal tissue is particularly suitable for forming the leaflet's peripheral region 22, since the peripheral region 22 is configured to contact a wall of a tubular body passage and promote tissue ingrowth into the peripheral region 22 from the wall of the tubular body passage.

Submucosal tissue may, for example, be prepared as described in U.S. Pat. Nos. 4,902,508; 5,554,389; and 6,206,931. Again, it should be understood that submucosa can be derived from any suitable organ or other biological structure, including for example, submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. Thereafter, the submucosa can be assembled into tissue segments (e.g., sheets, strands, and other shapes) or stored for later processing if desired.

Tissue ingrowth-receptive peripheral material may also be derived from any of a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

The remodelable ECM or other tissue ingrowth-receptive material may be manipulated before or after the leaflet 20 is assembled. For example, the material may be cut, trimmed, sterilized, and/or treated with one or more property modifiers. In certain embodiments, ECM material is crosslinked before or after any preliminary processing and/or storage. Crosslinking tends to fix ECM material in the shape imposed during the crosslinking process. However, because certain crosslinking agents and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Following any crosslinking, the material can be further processed, which can involve additional chemical and/or mechanical manipulation of the material, as well as processing the material into the desired peripheral region 22 assembly.

Crosslinking, in addition to providing mechanical stabilization (e.g., by anchoring the collagen fibrils and preventing enzymatic degradation of the tissue), can decrease or eliminate antigens in the tissue. Glutaraldehyde, formaldehyde or a combination thereof is typically used for fixation, but other fixatives can be used, such as epoxides, epoxyamines, diimides and other difunctional/polyfunctional aldehydes. In particular, aldehyde functional groups are highly reactive with amine groups in proteins, such as collagen. Epoxyamines are molecules that generally include both an amine moiety (e.g. a primary, secondary, tertiary, or quaternary amine) and an epoxide moiety. The epoxyamine compound can be a monoepoxyamine compound and/or a polyepoxyamine compound.

In addition to being crosslinked, the material can be treated (e.g., brought into contact, impregnated, coated, etc.) with one or more desirable compositions, such as anticoagulants (e.g., heparin), growth factors or other desirable property modifiers, to modify the tissue properties. Specifically, the tissue can be treated with an anticalcification agent to reduce calcification of the tissue following implantation and/or to encourage tissue remodeling. In certain embodiments, a calcification reducing agent is contacted with the material before or after crosslinking. Suitable calcification reducing agents include, for example, alcohols, such as ethanol and propylene glycol, detergents (e.g., sodium dodecyl sulfate), toluidine blue, diphosphonates, and multivalent cations, especially $Al^{+3}$, $Mg^{+2}$ or $Fe^{+3}$, or corresponding metals that can oxidize to form the multivalent metal cations.

Additionally, to encourage ingrowth of viable cells, the tissue can be treated to reduce or eliminate toxicity associated with aldehyde crosslinking and/or associated with compounds that stimulate the infiltration of the tissue by desirable cells. Further, the tissue can be crosslinked with dialdehydes or the like to reduce or eliminate any cytotoxicity. Suitable compounds for reduction of aldehyde cytotoxicity include, for example, amines, such as amino acids, ammonia/ammonium, sulfates, such as thiosulfates and bisulfates, surfactants and combinations thereof.

As prepared, a submucosa or other ECM material may optionally retain various bioactive components native to the source tissue. For example, the ECM material may include one or more growth factors, such as basic fibroblast growth factor (FGF-2), transforming growth factor beta (TGF-beta), epidermal growth factor (EGF), and/or platelet derived growth factor (PDGF). Further, the submucosa or other ECM material of the present invention may include other biological materials, such as heparin, heparin sulfate, hyaluronic acid, fibronectin and the like. Thus, generally speaking, the ECM material may include a bioactive component that induces, directly or indirectly, a cellular response, such as a change in cell morphology, proliferation, growth, protein or gene expression, which again, is desirable for promoting tissue ingrowth into the peripheral region 22 from the wall of a tubular body passage.

In addition to, or as an alternative to, the inclusion of such native bioactive components, non-native bioactive components, such as those synthetically produced by recombinant technology or other methods, may be incorporated into the ECM material. The addition of a non-native component, e.g., a growth factor, with a tissue matrix may involve direct attachment, application of a coating, including an adhesive or binder, or chemical binding, involving a binding agent. Further, these non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics, anti-thrombotic agents such as heparin, or other useful therapeutic substances. These substances may be applied to the ECM material as a premanufactured step, immediately prior to the procedure (e.g. by soaking the material in a solution containing a suitable antibiotic such as cefazolin), or during or after engraftment of the material in the patient.

The ECM material used in the invention is preferably highly purified, for example as described in U.S. Pat. No. 6,206,931. Thus, the preferred material will exhibit an endotoxin level of less than about 12 endotoxin units (EU) per gram, more preferably less than about 5 EU per gram, and most preferably less than about 1 EU per gram. As additional preferences, the ECM material may have a bioburden of less than about 1 colony forming units (CFU) per gram, and more preferably less than about 0.5 CFU per gram. Fungus levels are desirably low as well, for example less than about 1 CFU per gram, and more preferably less than about 0.5 CFU per gram. Nucleic acid levels are preferably less than about 5 µg/mg, and more preferably less than about 2 µg/mg, while virus levels are preferably less than about 50 plaque forming units (PFU) per gram, and more preferably less than about 5 PFU per gram. These and additional properties of submucosa taught in U.S. Pat. No. 6,206,931 may be characteristic of the ECM material used in the present invention.

Continuing with FIG. 1, the leaflet's inner region 21 and peripheral region 22 are attached with sutures 23, although it should be noted that various modes of attachment (e.g., adhesives, fasteners, tissue welding or fusion using heat and/or pressure, chemical crosslinking, etc.), alone or in combination, could be used.

Figure 2:
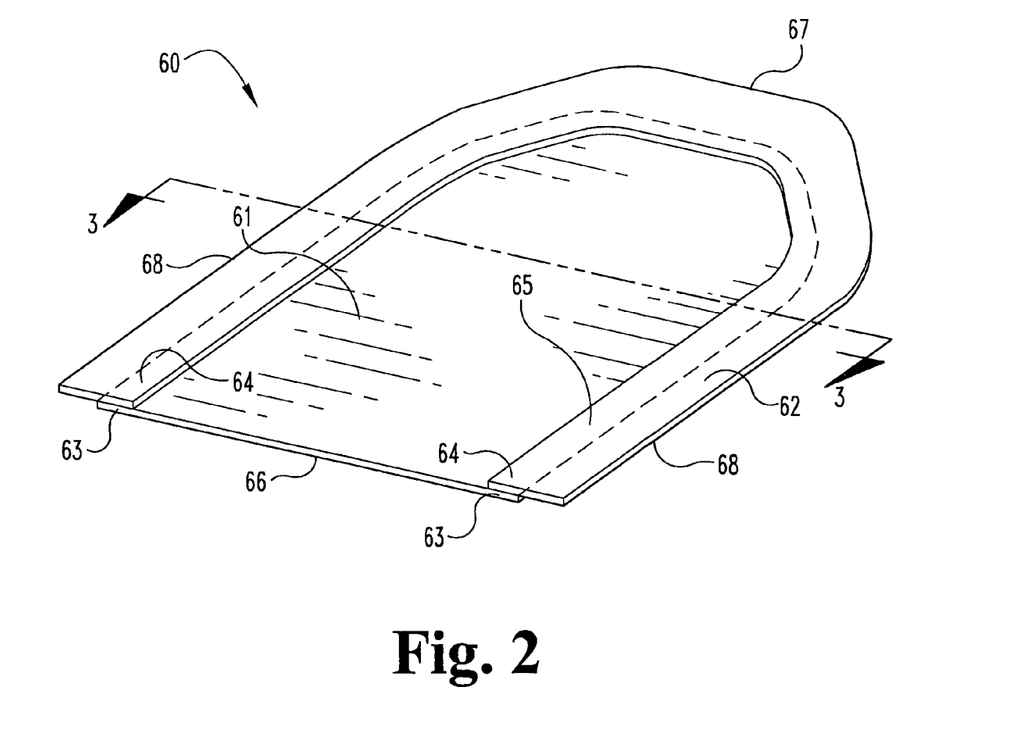
FIG. 2 is a perspective view of a medical valve leaflet that has a first segment, which is attached to and partially overlapped by a second segment.
Figure 3:
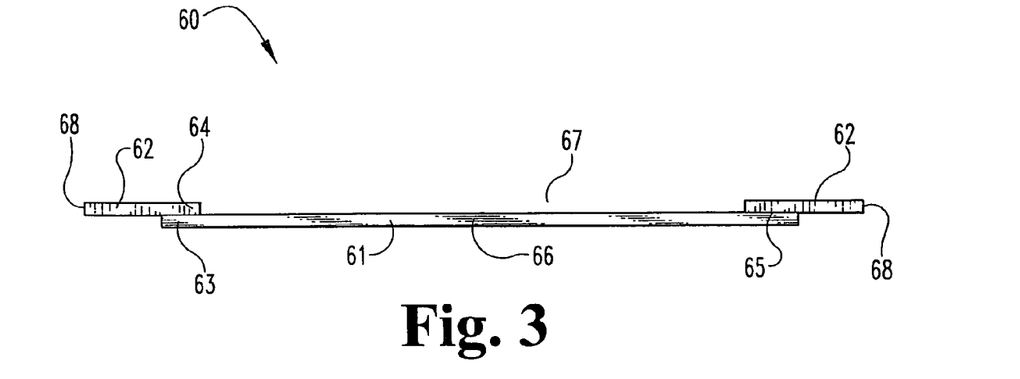
FIG. 3 provides a cross-sectional view of the medical valve leaflet of FIG. 2 along the view line 3-3 shown in FIG. 2.

FIGS. 2 and 3 depict a medical valve leaflet 60 that includes a first segment 61 and a second segment 62. The first segment 61 has a first segment boundary portion 63, and the second segment 62 has a second segment boundary portion 64. The second segment boundary portion 64 overlaps the first segment boundary portion 63, creating a segment overlap area 65. The first segment 61 and second segment 62 are bonded together at or near the segment overlap area 65. The first segment 61 is formed with a flexible synthetic polymer, while the second segment 62 is formed with a flexible material to promote tissue ingrowth.

Continuing with FIGS. 2 and 3, the leaflet 60 has a first end 66, a second end 67, and sides 68. Portions of the first segment 61 and second segment 62 form the leaflet's first end 66, while at least a portion of the second segment 62 forms the leaflet's second end 67 and sides 68. The second segment 62 is configured to contact a wall of a tubular body passage and thereby promote tissue ingrowth into the second segment 62 from the wall of the tubular body passage.

The leaflet 60 can be used in a variety of ways, including but not limited to the uses disclosed above for the leaflet of FIG. 1. Also, the size and shape of the first segment 61 and second segment 62 can vary depending on the size and shape of the leaflet 60 being assembled. Again, the size of the assembled leaflet 60 should be suitable for implantation into a tubular body passage. Further, the first segment 61 and second segment 62 should be formed with materials that are generally biocompatible (i.e., are non-toxic and non-carcinogenic, and do not induce a significant immunological response, etc.).

After the leaflet 60 is assembled, it can be manipulated to alter its shape, size, and/or configuration, etc. For example, portions of a leaflet could be removed in one or more areas, in the initial manufacture or by subsequent processing, as necessary to provide a specific elasticity profile for a particular application. Also, it should be appreciated that the medical valve leaflet 60 of FIG. 2 could be formed without the segment overlap area 65. In this case, the second segment boundary portion 64, instead of overlapping the first segment boundary portion 63, could butt up against it.

Figure 4:
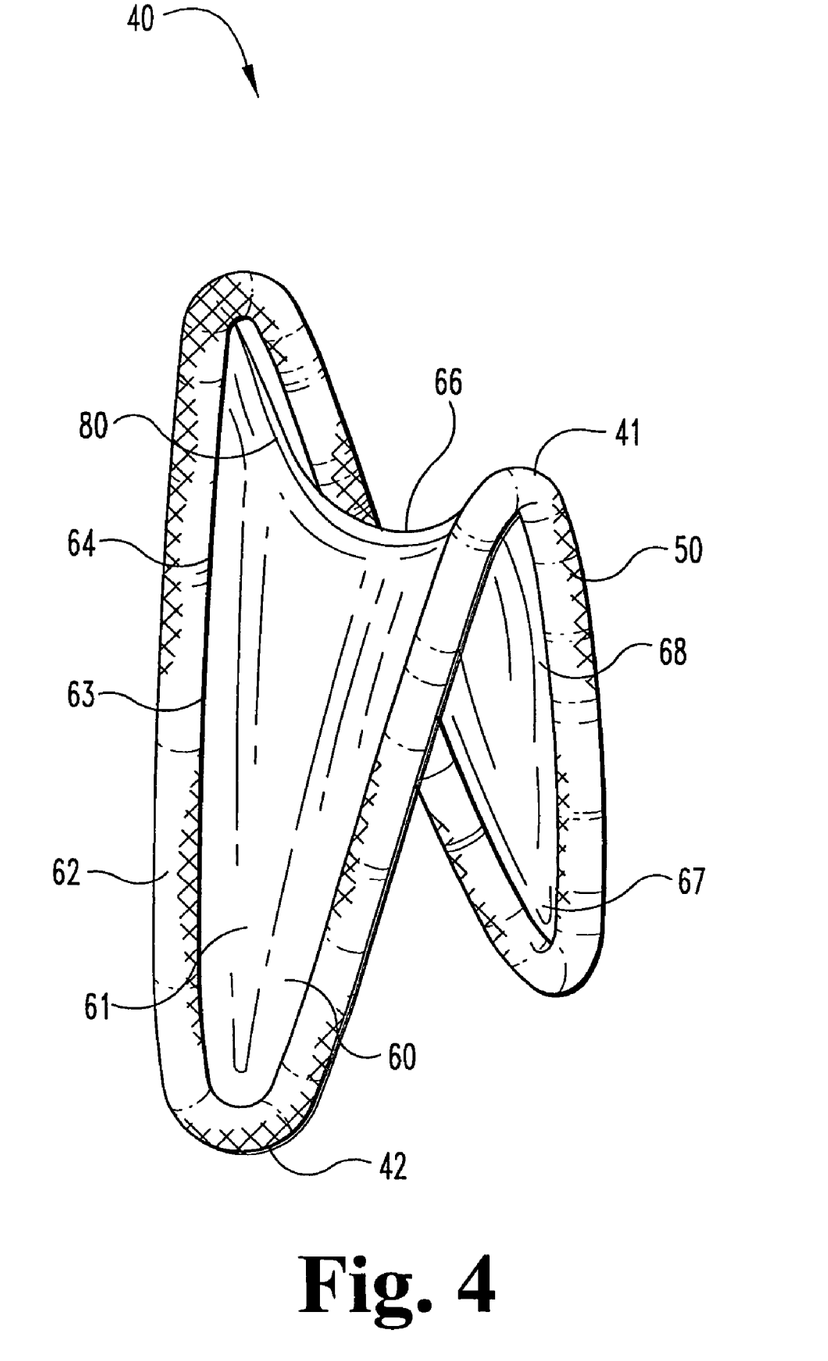
FIG. 4 is a perspective view of a prosthetic valve that includes a pair of composite leaflets attached to a frame.

FIG. 4 is a perspective view of a prosthetic valve 40, which includes a pair of the composite leaflets 60 attached to a metallic frame 50. The leaflets' second ends 67 and sides 68 wrap around the frame 50 so that the leaflets' second segments 62 envelop the frame 50. (In FIG. 4, the leaflets' second segments 62 completely surround the frame 50.) The second segments 62 are configured to contact a wall of a tubular body passage and thereby promote tissue ingrowth into the second segments 62 from the wall of the tubular body passage.

Figure 6:
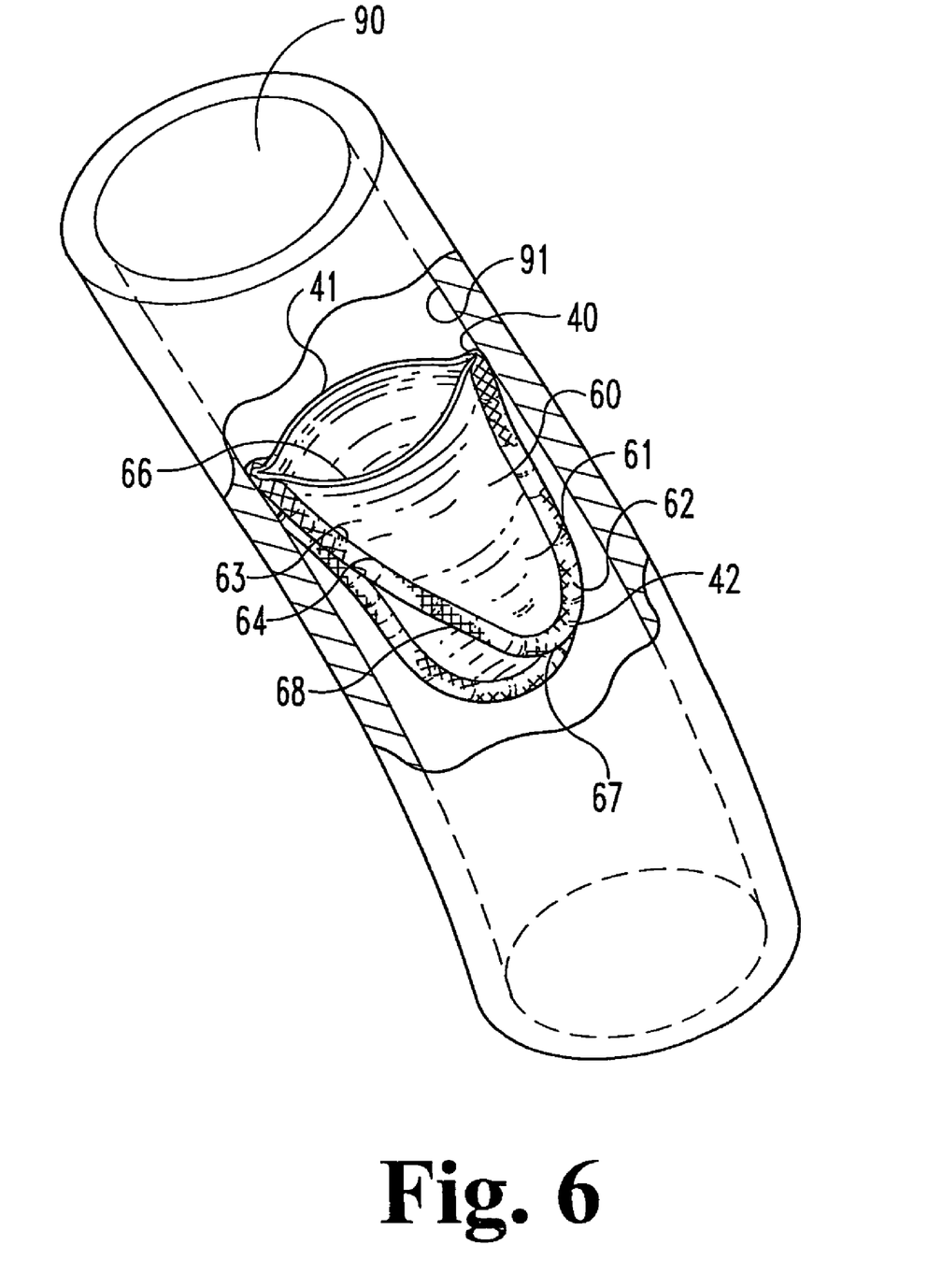
FIG. 6 is a perspective view of the valve of FIG. 4 implanted in a vessel or duct of a patient, the valve in an open, flow-conducting configuration.
Figure 7:
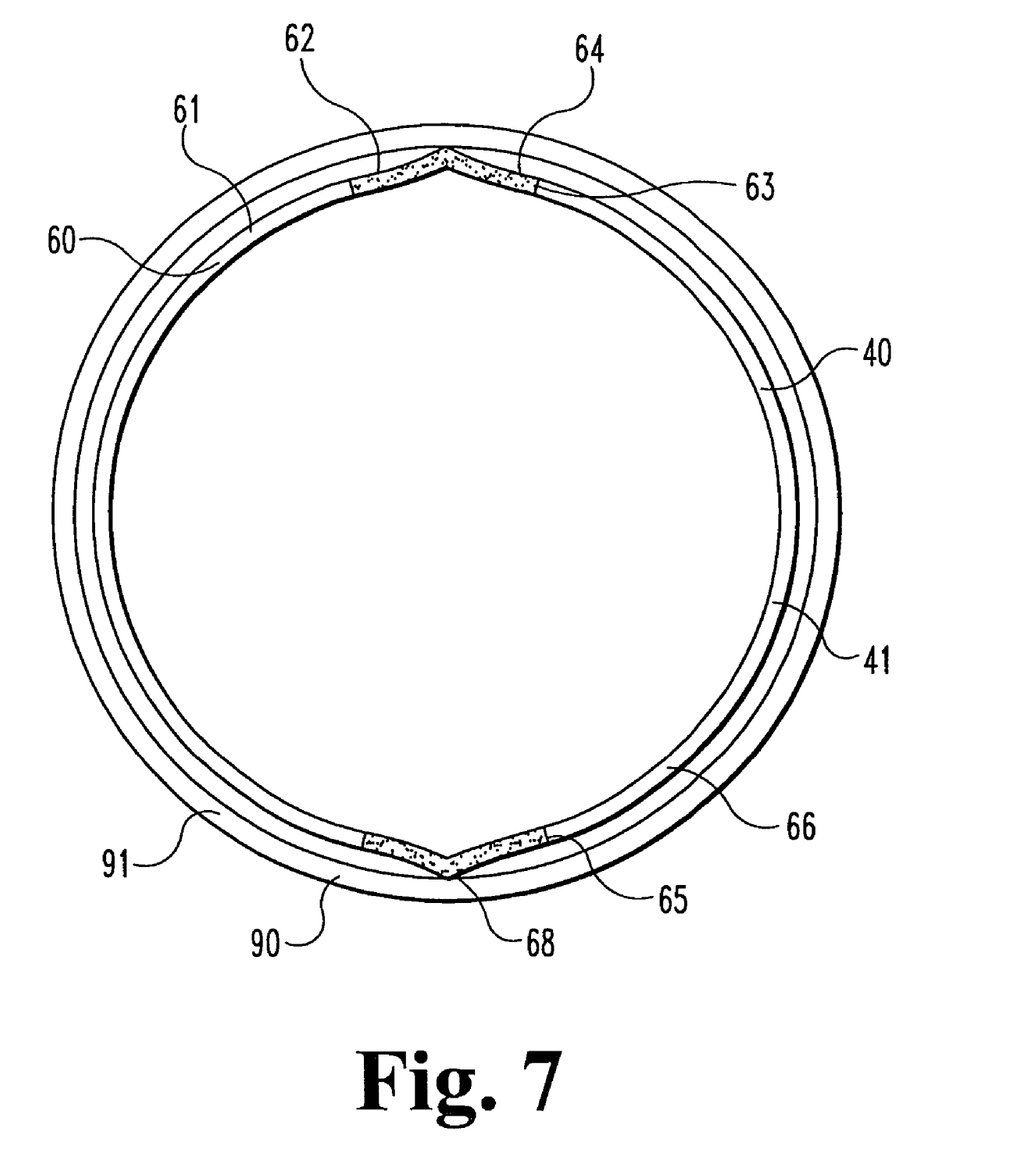
FIG. 7 shows a top view of the valve of FIG. 6.
Figure 8:
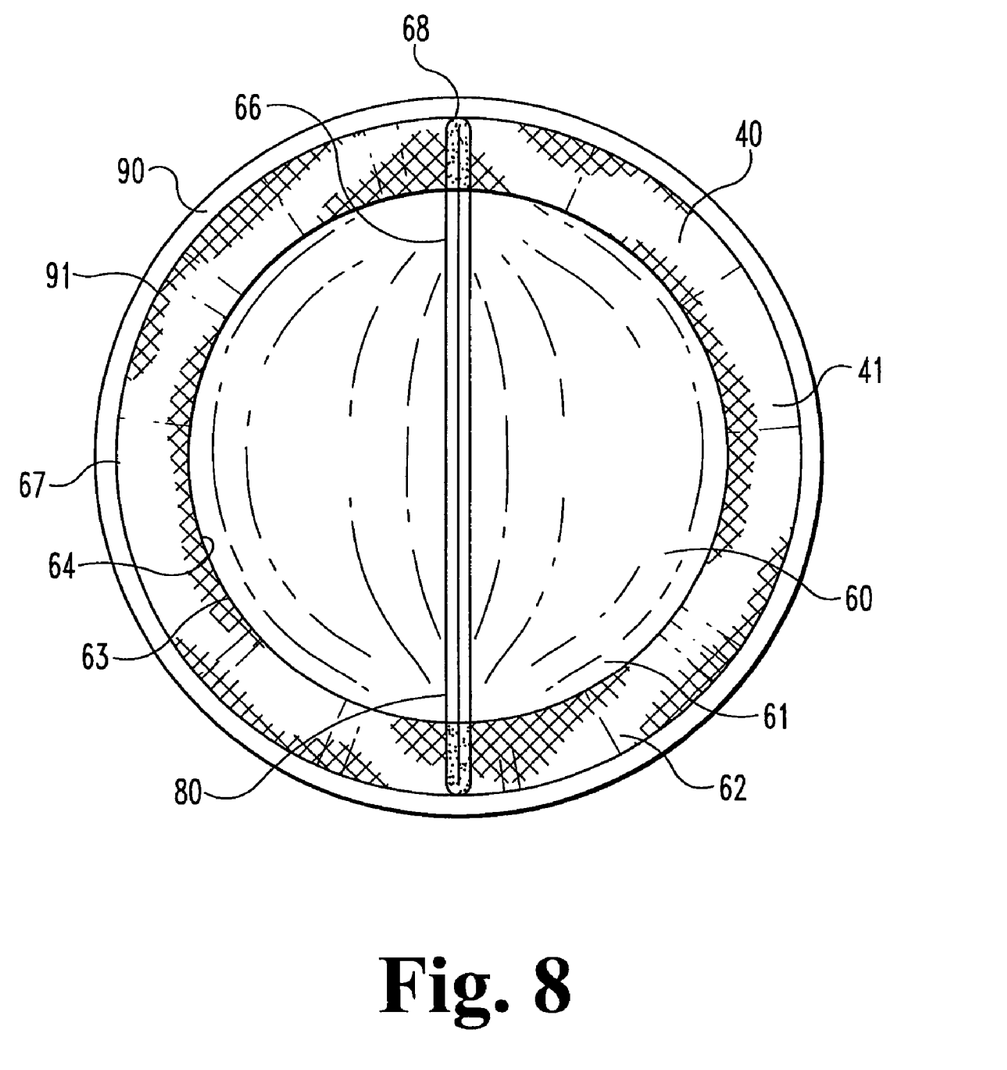
FIG. 8 shows a top view of the valve of FIG. 4 implanted in a vessel or duct of a patient, the valve in a closed, flow-restricting configuration.

When the valve is deployed in a tubular body passage (e.g., at a site within the venous or arterial system), the leaflets 60 move back and forth in response to changes in fluid dynamic pressure. When fluid is stagnant or flowing through the bodily passageway in a normal, forward direction, the leaflets 60 remain mostly open (as shown in FIGS. 6 and 7). When fluid begins to flow in a direction opposite its normal, forward flow, the leaflets 60 move toward a closed position (as shown in FIGS. 4 and 8). Further, it should be appreciated that although the embodiment of FIG. 4 provides a bi-leaflet valve, the invention disclosed herein provides for prosthetic valves having a total of one, two, three, or any suitable number of leaflets. For example, bi-leaflet valves may prove advantageous in low-flow venous situations, whereas tri-leaflet embodiments may be more suitable for replacing or supplementing certain diseased heart valves (e.g. native tri-leaflet heart valves).

Figure 5:
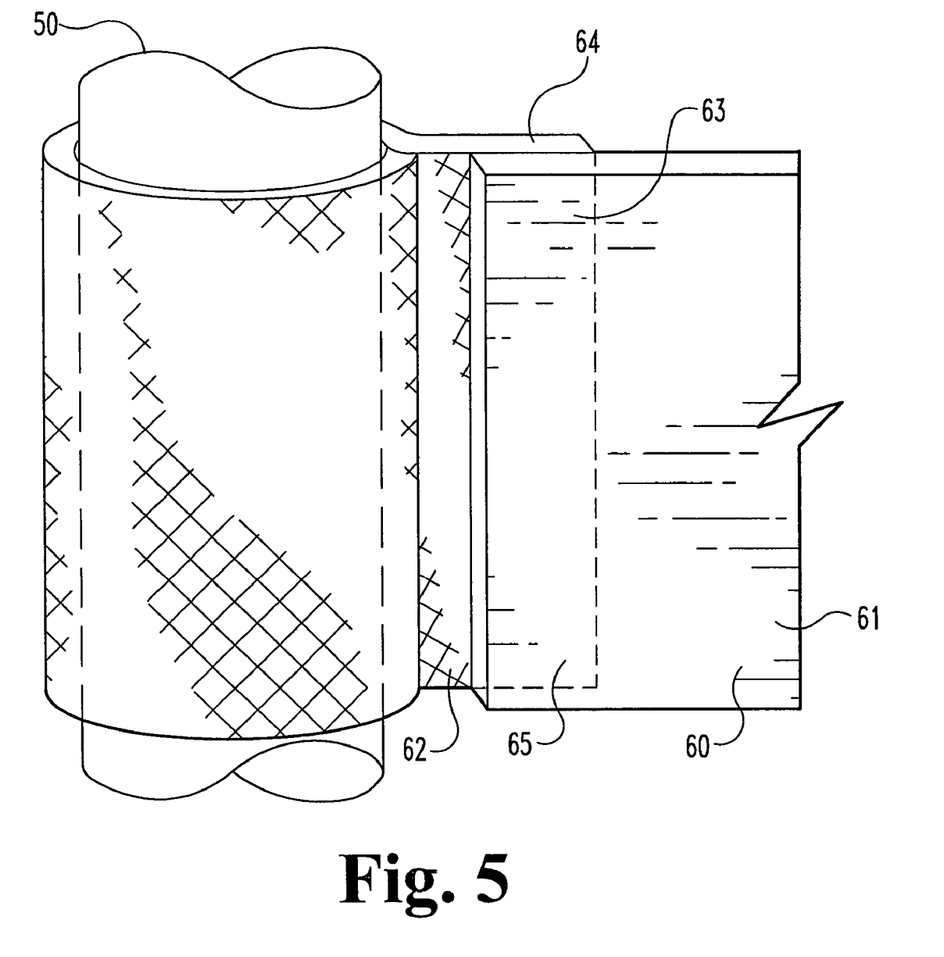
FIG. 5 is a partial, perspective view of the prosthetic valve of FIG. 2, showing a portion of one of the composite leaflets wrapped around and attached to the frame.

FIG. 5 is a partial, perspective view of the valve of FIG. 4, showing a portion of one of the leaflets attached to the frame 50. Here, the second segment 62 is wrapped around the frame 50 and attached to itself to secure the leaflet 60 to the frame 50. Although not shown in this embodiment, sutures could be used to attach the second segment 62 to itself. The second segment 22, in addition to being attached to itself, could also be glued directly to the frame 50. However, it should be noted that several modes of attachment (e.g., sutures, adhesives, fasteners, tissue welding using heat and/or pressure, etc.), alone or in combination, could be used to attach the second segment 62 to itself or the frame 50.

Continuing with FIG. 4, it should be noted that after the prosthesis 40 is assembled, the leaflets 60 may optionally be manipulated to alter their shape, size, configuration, and/or orientation. For example, the leaflets may be chemically or otherwise treated to modify the flow dynamics within the prosthesis 40 so that bodily fluid collecting in pockets near the second ends 67 of the leaflets 60 is more likely to be flushed away or continually mixed with fresher incoming fluid.

In this embodiment, the composite leaflets 60 are attached to a bi-leaflet forming frame 50. However, it should be noted that the composite leaflets of the present invention could be attached to a variety of frames. The frame 50 depicted in FIG. 4 is only one of many different types of frames that could be utilized in the present invention. Any practical frame design or style could be used depending on the characteristics desired for a particular application.

The frame 50 depicted in FIG. 4 can be formed with a metallic material including but not limited to stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). However, it should be noted that a variety of other materials can be used to form the frame 50 depending on the characteristics desired for a particular application (e.g., weight, durability, collapsibility, etc.). For instance, the frame 50 could be formed with any of the materials used to form the composite leaflets 60 previously discussed (e.g., PTFE or SIS). Further, the material could be in the form of yarns, fibers, and/or resins, monofilament yarns, high tenacity polyester. Moreover, other materials may be used in the formation of the frame 50 including for example plastic, resin, polymer, woven, and fabric surgical materials, other conventional synthetic surgical materials, such as a shape-memory plastic, and/or combinations of such materials.

FIG. 6 shows the prosthetic valve 40 of FIG. 4 implanted into a bodily passageway 90 of a patient. Here, the valve is in an open, flow-conducting configuration. In practice, a surgeon can implant the valve 40 into a bodily passageway 90 (e.g., a vessel or duct), for example, by using a well-known transcatheter technique for implanting valvular prostheses. The prosthesis 40 has a first, annular end 41 and a second, annular end 42, with the normal, antegrade flow of blood typically traveling from the second or distal end 42 to the first or proximal end 41, the latter being located closest to the heart when, for example, the prosthesis is deployed at a venous site within the lower extremities of a patient.

As shown in FIG. 6, the leaflets' second ends 67 and sides 68 are wrapped around the frame 50 so that the leaflets' second segments 62 completely envelop the frame 50. (In another embodiment, the second segment 62 only envelops a portion of the frame 50.) This configuration allows the second segments 62 to contact at least a portion of the passageway's inner wall 91 and thereby receive and/or promote tissue ingrowth into the second segments 62 from the wall 91. The tissue ingrowth into the second segment 62 can, for example, facilitate the creation of a perimeter seal between the valve 40 and the inner wall 91. Also, the tissue ingrowth may serve to hold or fix the valve 40 at a general location within the passageway. Therefore, while portions of the valve 40 are adapted to move within the passageway to perform a particular function, e.g., the leaflets performing a valving function, the tissue ingrowth can generally prevent the valve as a whole from migrating from the implantation site and/or serve a sealing function.

FIG. 7 shows a top view of the valve 40 of FIG. 6. The open, flow-conducting configuration depicted is typically achieved when blood is stagnant or flowing through the bodily passageway 90 in a normal, forward direction. Here, the leaflets' first ends 66 are being forced away from each other and toward the vein wall 91 to form a conduit through which blood can flow.

FIG. 8 shows a top view of the valve 40 of FIG. 4 implanted into a bodily passageway 90 of a patient. Here, however, the valve 40 is in a closed, flow-restricting configuration, which is typically achieved when blood begins to flow in a direction opposite its normal, forward flow. In this case, the leaflets' first ends 66 are being forced away from the inner wall 91 and toward each other to form a closure or coaptation 80, which eliminates or greatly reduces back flow through the valve 40.

As highlighted in FIGS. 7 and 8, regardless of the valve's configuration (e.g., open or closed), at least a portion of the leaflets' second segments 62 remain in contact with the passageway's inner wall 91 and thereby promote tissue ingrowth into the second segments 62 from the wall 91.

Figure 9:
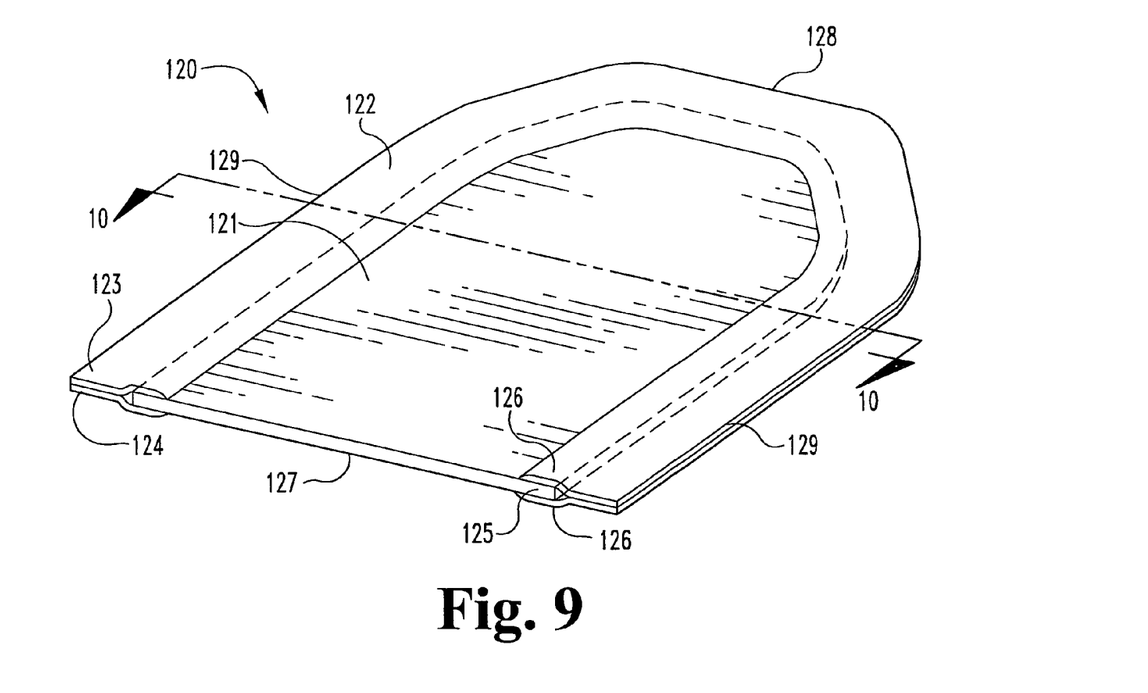
FIG. 9 is a perspective view of a medical valve leaflet that has a first segment and a second segment, where the second segment includes two layers of material that sandwich the first segment.
Figure 10:
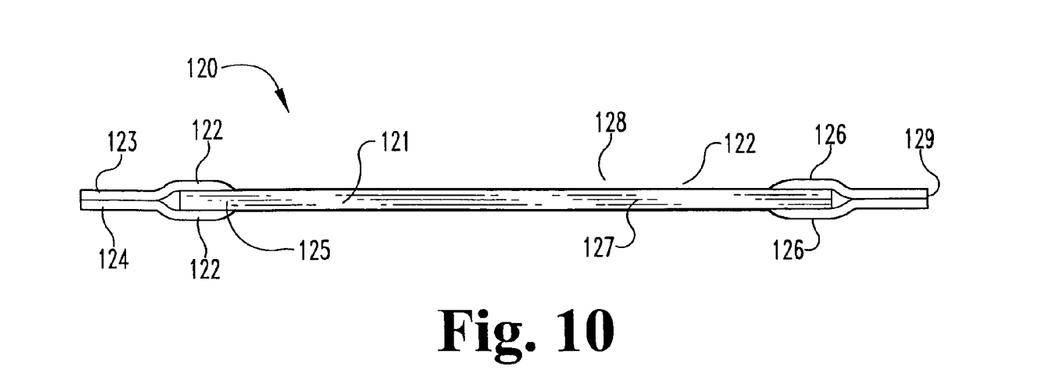
FIG. 10 provides a cross-sectional view of the medical valve leaflet of FIG. 9 along the view line 10-10 shown in FIG. 9.
Figure 11:
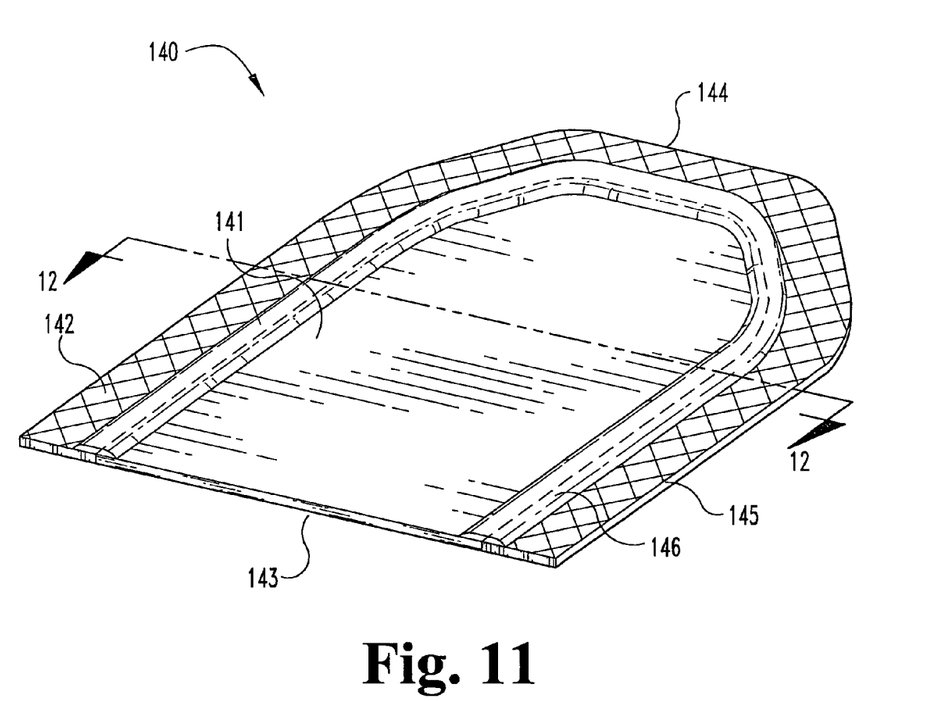
FIG. 11 is a perspective view of a medical valve leaflet that includes a linking segment to help connect the leaflet's inner and peripheral regions.

FIGS. 9 and 10 depict a medical valve leaflet 120 that has a first segment 121 and a second segment 122. The second segment 122 includes a first layer 123 and a second layer 124. The first segment 121 has a first segment boundary portion 125, and the second segment 122 has second segment boundary portions 126. The first segment boundary portion 125 is attached to the second segment boundary portions 126, with the second segment's first layer 123 and second layer 124 sandwiching the first segment boundary portion 125. The first segment 121 is formed with a non-remodelable material, while the second segment 122 is formed with a remodelable material to promote tissue ingrowth.

Continuing with FIGS. 9 and 10, the leaflet 120 has a first end 127, a second end 128, and sides 129. Portions of the first segment 121 and second segment 122 form the leaflet's first end 127, while at least a portion of the second segment 122 forms the leaflet's second end 128 and sides 129. The second segment 122 is configured to contact a wall of a tubular body passage and thereby promote tissue ingrowth into the second segment 122 from the wall of the tubular body passage. After the leaflet 120 is assembled, it can be manipulated to alter its shape, size, and/or configuration, etc.

The leaflet 120 can be used in a variety of ways, including but not limited to the uses disclosed above for the leaflet of FIG. 1. Also, the size and shape of the first segment 121 and second segment 122 can vary depending on the size and shape of the leaflet 120 being assembled. Again, the size of the assembled leaflet 120 should be suitable for implantation into a tubular body passage. Further, it is desirable that the first segment 121 and second segment 122 be formed with materials that are generally biocompatible.

It should further be appreciated that the second segment 122 is not limited to being formed with two layers of material. In certain embodiments, the second segment 122 is formed with a single sheet of material that is wrapped around the first segment boundary portion 125 and attached to opposite surfaces of the first segment 121. In these embodiments, a hollow passageway may be formed between the first segment 121 and second segment 122 that runs the length of the leaflet's second end 128 and sides 129. If the leaflet 120 is associated with a frame (e.g., to form a prosthetic valve), a portion of the frame can be positioned within the hollow passageway, either before or after the composite leaflet 120 is formed.

It will also be understood that in certain embodiments of the invention, one or more leaflets of the present invention (e.g., the leaflet 120) can be associated with one or more removable frame elements. For example, composite leaflet 120 could be associated with a removable frame element as described in International Patent Application serial No. PCT/US2004/008176 filed Mar. 17, 2004, published Sep. 30, 2004, as WO2004/082528, which is hereby incorporated by reference. In this manner, the valve construct including the frame element(s) and leaflet(s) can be implanted (e.g. percutaneously) in a bodily passageway of a patient, such as a vein or artery, allowed to indwell for a sufficient period of time to achieve tissue ingrowth into the second segment 122 (e.g. for site fixation and/or sealing), and the removable frame element(s) thereafter retrieved (e.g. percutaneously). The resulting long-term valve in the patient can thereby include fewer or no associated frame elements.

Figure 12:
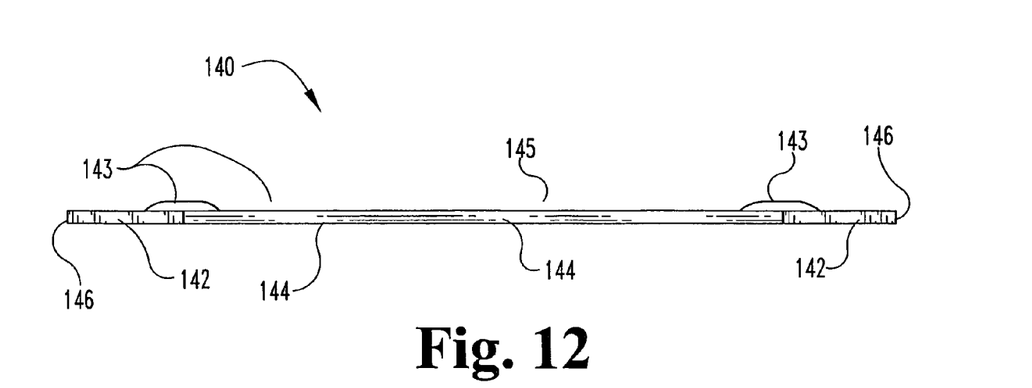
FIG. 12 provides a cross-sectional view of the medical valve leaflet of FIG. 11 along the view line 12-12 shown in FIG. 11.

FIGS. 12 and 13 depict a medical valve leaflet 140 that has a flexible inner region 141 and a flexible peripheral region 142. The leaflet 140 further includes a linking segment 143 to help connect the inner region 141 to the peripheral region 142. The inner region 141 is formed with a synthetic polymeric material, while the peripheral region 142 is formed with a remodelable material to promote tissue ingrowth. In this embodiment, the linking segment 143 is formed with SIS, although any of the synthetic polymeric or remodelable materials disclosed in this application, alone or in combination, could be used.

Continuing with FIGS. 12 and 13, the leaflet 140 has a first end 144, a second end 145, and sides 146. Portions of the inner region 141, peripheral region 142, and linking segment 143 form the leaflet's first end 144, while at least a portion of the peripheral region 142 forms the leaflet's second end 145 and sides 146. The peripheral region 142 is configured to contact a wall of a tubular body passage and thereby promote tissue ingrowth into the peripheral region 142 from the wall of the tubular body passage. After the leaflet 140 is assembled, it can be manipulated to alter its shape, size, and/or configuration, etc.

The leaflet 140 can be used in a variety of ways, including but not limited to the uses disclosed above for the leaflet of FIG. 1. Also, the size and shape of the inner region 141 and peripheral region 142 can vary depending on the size and shape of the leaflet 140 being assembled. Again, the size of the assembled leaflet 140 should be suitable for implantation into a tubular body passage. Further, it is desirable that the inner region 141 and peripheral region 142 be formed with materials that are generally biocompatible.

With respect to the leaflet structures disclosed herein, it will be understood that the segments or regions with differing properties can result from the attachment of differing materials to one another, a differential treatment of a given material, or other techniques. In certain embodiments, for example, a temporary or permanent coating that promotes tissue ingrowth may be applied to peripheral and/or other regions of a relatively tissue ingrowth-resistant leaflet material that are to contact the walls of the bodily passage. In still other embodiments, where a tissue ingrowth receiptive and/or promoting leaflet material is used, a central or other region to extend into the lumen of the bodily passage can be treated to reduce or eliminate tissue ingrowth properties. For instance, in the case of a remodelable leaflet material, such as a remodelable ECM, such a central or lumen-residing region can be crosslinked or otherwise treated to an extent that reduces or removes the remodelable properties and renders the material non-resorbable.

Yet other embodiments of the invention provide methods for treating patients. The methods include providing one of the prosthetic valves or leaflet structures of the present invention and implanting the valve(s) or leaflet(s) in a tubular body passage of a patient and in particular a human.

In further embodiments, the present invention provides sterilized, medical products, the products comprising at least one of the valve leaflets or valve prostheses of the present invention in any suitable state (e.g., hydrated, dehydrated, or partially dehydrated). The product can be dehydrated or partially dehydrated by any means known in the art (e.g., lyophilization or air dried). If a product of the present invention is stored in a dehydrated state, it is preferred that it retains all of its biological and mechanical properties (e.g., shape, density, flexibility, etc.) upon rehydration. In some embodiments, a medical product is packaged. The materials and other properties of the packaging will be selected accordingly. For example, the packaging may contain visible indicia with regard to its contents. Such indicia may include the dimensions of the valve leaflet or prosthetic valve, the type of materials used to form the product, and the product's physical state. In certain embodiments, the packaging is resealable. In other embodiments, instructions for use are included with the medical product. Sterilization will be achieved via irradiation, ethylene oxide gas, or another suitable sterilization technique.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A medical valve prosthesis for implantation within a bodily passage, the valve prosthesis comprising at least a first valve leaflet, the first valve leaflet including an outer portion configured to reside adjacent a wall of the bodily passage upon implantation, the first valve leaflet further including a composite leaflet body extending from said outer portion so as to reside away from said wall in a lumen of the bodily passage upon implantation, the composite leaflet body including a flexible inner region formed entirely with a synthetic polymeric sheet material, and further including a flexible peripheral region attached to said flexible inner region and formed with a remodelable sheet material, said flexible inner region abutting or partially overlapping said flexible peripheral region with said synthetic polymeric sheet material providing a free upper edge of the composite leaflet body, said free upper edge having a single layer thickness provided by said synthetic polymeric sheet material, with said single layer thickness extending between an exposed top face and an exposed bottom face of the synthetic polymeric sheet material which are both exposed in the composite leaflet body as a whole, wherein said flexible peripheral region is configured to contact a wall of the bodily passage upon implantation so as to promote cellular invasion and ingrowth into the remodelable sheet material from the wall of the bodily passage, and wherein said flexible inner region is configured to reside in the bodily passage upon implantation so that fluid flowing through the bodily passage can contact said exposed top face and said exposed bottom face of said synthetic polymeric sheet material.

2. The medical valve prosthesis of claim 1 wherein said flexible inner region includes material that does not overlap said flexible peripheral region.

3. The medical valve prosthesis of claim 2, wherein said remodelable sheet material comprises a remodelable extracellular matrix material.

4. The medical valve prosthesis of claim 3 wherein said remodelable extracellular matrix material comprises submucosa.

5. The medical valve prosthesis of claim 4, wherein said remodelable extracellular matrix material comprises porcine submucosa.

6. The valve prosthesis of claim 5, wherein said porcine submucosa comprises small intestine submucosa, urinary bladder submucosa, or stomach submucosa.

7. The medical valve prosthesis of claim 1, also including a frame attached to said first valve leaflet.

8. The medical valve prosthesis of claim 1 having at least two valve leaflets.

9. A composite medical valve leaflet for implantation within a tubular body passage, the composite medical valve leaflet comprising:
    a flexible inner region; and
    a flexible outer region attached to said flexible inner region,
    said flexible inner region providing a free upper edge in the composite medical valve leaflet, said free upper edge having a single layer thickness that is provided by a single layer of a synthetic polymeric sheet material, said single layer thickness extending between an exposed top face and an exposed bottom face of said synthetic polymeric sheet material which are both exposed in the composite medical valve leaflet as a whole,
    said flexible peripheral region comprising a remodelable sheet material having an edge that abuts or partially overlaps said synthetic polymeric sheet material;
    said peripheral region configured to contact a wall of the tubular body passage upon implantation so as to promote tissue ingrowth into the remodelable material from the wall of the tubular body passage while allowing said synthetic polymeric sheet material to extend out into the lumen of the tubular body passage for contacting and modifying fluid flow through the body passage, wherein said synthetic polymeric sheet material extends beyond said edge of said remodelable sheet material such that fluid flowing through the body passage can contact said exposed top face and said exposed bottom face of said synthetic polymeric sheet material.

10. The medical valve leaflet of claim 9, wherein said remodelable sheet material comprises a remodelable extracellular matrix material.

11. The medical valve leaflet of claim 10, wherein said remodelable extracellular matrix material comprises submucosa.

12. The medical valve leaflet of claim 11, wherein said remodelable extracellular matrix material comprises porcine submucosa.

13. The medical valve leaflet of claim 9, wherein said inner region is attached to said peripheral region with an adhesive.

14. The medical valve leaflet of claim 9, which is configured for implantation in a vascular vessel.

15. The medical valve leaflet of claim 14, which is configured for implantation in a venous vessel.

16. The medical valve leaflet of claim 9, wherein said inner region is attached to said peripheral region with sutures.

17. A medical valve leaflet, comprising:
    a first flexible sheet segment formed with a non-remodelable sheet material and including a first segment boundary portion, said non-remodelable sheet material having a thickness that extends between an exposed top face and an exposed bottom face of the non-remodelable sheet material; and a second flexible sheet segment formed with a remodelable material and including a second segment boundary portion, wherein the first segment boundary portion is attached to the second segment boundary portion to form a composite leaflet structure for implantation in a tubular body passage, with the first segment boundary portion abutting or partially overlapping the second segment boundary portion, the composite leaflet structure configured such that the first segment boundary portion is attached to the second segment boundary portion in one or more attachment locations to occur out away from a wall of the tubular body passage when the composite leaflet structure is implanted in the tubular body passage, wherein said non-remodelable sheet material provides a free upper edge in the composite leaflet structure with the exposed top face and the exposed bottom face of the non-remodelable sheet material both being exposed in the composite leaflet structure as a whole, and wherein said first flexible sheet segment is configured to extend out into the tubular body passage beyond said second flexible sheet segment when the medical valve leaflet is implanted in the tubular body passage such that fluid flowing through the tubular body passage can contact said exposed top face and said exposed bottom face of said non-remodelable sheet material.

18. The medical valve leaflet of claim 17, wherein said first flexible sheet segment overlaps said second flexible sheet segment.

19. The medical valve leaflet of claim 17, wherein said first flexible sheet segment is formed with a synthetic polymeric material.

20. The medical valve leaflet of claim 17, wherein said second flexible sheet segment includes two layers of material.

21. The medical valve leaflet of claim 17, wherein said second flexible sheet segment is configured to contact a wall of a tubular body passage and is receptive to tissue ingrowth into said second flexible sheet segment from the wall of the tubular body passage.

22. The medical valve leaflet of claim 17, wherein said first flexible sheet segment does not overlap said second flexible sheet segment.

23. The medical valve leaflet of claim 17, wherein said second flexible sheet segment is collagenous.

24. The medical valve leaflet of claim 17, wherein said second flexible sheet segment comprises an extracellular matrix material.

25. The medical valve leaflet of claim 24, wherein said extracellular matrix material comprises submucosa, serosa, pericardium, dura mater, peritoneum, or dermal collagen.

26. A medical valve prosthesis implantable within a tubular body passage for modifying fluid flow through the tubular body passage, the medical valve prosthesis comprising:

a composite valve leaflet, comprising:
  a flexible inner region formed entirely with a non-remodelable sheet material, wherein the non-remodelable sheet material provides a free upper edge of the composite valve leaflet, said free upper edge having a thickness that extends between an exposed top face and an exposed bottom face of the non-remodelable sheet material which are both exposed in said composite valve leaflet as a whole; and
  a flexible peripheral region extending from at least a portion of said flexible inner region, said flexible peripheral region comprising a remodelable sheet material having an edge that abuts or partially overlaps said non-remodelable sheet material;

said remodelable sheet material configured to extend outwardly into the tubular body passage lumen for attachment to the flexible inner region while maintaining contact with a wall of the tubular body passage when the valve prosthesis is implanted in the tubular body passage, wherein said flexible peripheral region is configured to promote tissue ingrowth into said remodelable sheet material from the tubular body passage while allowing said non-remodelable sheet material to extend out into the tubular body passage beyond said edge of the remodelable sheet material so that fluid flowing through the tubular body passage can contact said exposed top face and said exposed bottom face of said non-remodelable sheet material.

27. The medical valve prosthesis of claim 26 configured for implantation within a tubular body passage in the absence of a frame.

28. A prosthetic medical valve device configured for implantation within a bodily passage, the medical valve device comprising:

a plurality of valve leaflets that together provide a composite valve structure that is configured to reside in a lumen of the bodily passage for modifying flow through the passage, the composite valve structure comprising:
  an inner valve region formed entirely with a synthetic polymeric sheet material, said synthetic polymeric sheet material providing a free upper edge of each of said plurality of valve leaflets, said free upper edge having a thickness that extends between an exposed top face and an exposed bottom face of the synthetic polymeric sheet material which are both exposed in the composite valve structure as a whole; and
a peripheral valve region comprising a remodelable material, the peripheral valve region including at least one flexible sheet segment that is configured to extend outwardly into the bodily passage lumen for attachment to the inner valve region while maintaining contact with a wall of the bodily passage when the valve device is implanted in the bodily passage,
wherein said peripheral valve region is configured to promote tissue ingrowth into said remodelable material from a wall of the bodily passage while allowing said synthetic polymeric sheet material to extend out into the bodily passage for contacting and modifying fluid flow through the bodily passage, wherein said synthetic polymeric sheet material extends beyond an edge of the remodelable material so that fluid flowing through the bodily passage can contact said exposed top face and said exposed bottom face of said synthetic polymeric sheet material.

* * * * *